(12) United States Patent
Ahn et al.

(10) Patent No.: US 12,396,697 B2
(45) Date of Patent: Aug. 26, 2025

(54) BLOOD VESSEL IMAGE CALIBRATION METHOD AND DEVICE

(71) Applicant: Medipixel, Inc., Seoul (KR)

(72) Inventors: Jung-Min Ahn, Seoul (KR); Young Rak Choi, Seoul (KR); Hwi Kwon, Seoul (KR); Min Hyung Kim, Seoul (KR)

(73) Assignee: Medipixel, Inc., Seoul (KR)

( * ) Notice: Subject to any disclaimer, the term of this patent is extended or adjusted under 35 U.S.C. 154(b) by 0 days.

(21) Appl. No.: 18/861,984

(22) PCT Filed: May 2, 2023

(86) PCT No.: PCT/KR2023/005946
§ 371 (c)(1),
(2) Date: Oct. 31, 2024

(87) PCT Pub. No.: WO2023/214762
PCT Pub. Date: Nov. 9, 2023

(65) Prior Publication Data
US 2025/0169784 A1    May 29, 2025

(30) Foreign Application Priority Data

May 2, 2022 (KR) .......... 10-2022-0054209
Apr. 28, 2023 (KR) .......... 10-2023-0056529

(51) Int. Cl.
*A61B 6/50* (2024.01)
*A61B 6/00* (2024.01)

(52) U.S. Cl.
CPC ............ *A61B 6/504* (2013.01); *A61B 6/4441* (2013.01)

(58) Field of Classification Search
CPC ....... A61B 6/504; A61B 6/4441; A61B 6/503; A61B 6/581–589
See application file for complete search history.

(56) References Cited

U.S. PATENT DOCUMENTS 6,731,283 B1    5/2004    Navab
9,380,991 B2    7/2016    Wang et al.
(Continued)

FOREIGN PATENT DOCUMENTS

JP    H09-149902 A    6/1997
JP    2004-208714 A    7/2004
(Continued)

OTHER PUBLICATIONS

CAAS Workstation 7.5. User Manual. Pie Medical Imaging B.V. 2017, pp. 12-13.
(Continued)

*Primary Examiner* — Keith M Raymond
*Assistant Examiner* — Milton Truong
(74) *Attorney, Agent, or Firm* — Banner & Witcoff, Ltd.

(57) ABSTRACT

An electronic device for processing a blood vessel image according to an embodiment may include: an arc-shaped C-arm open toward the isocenter; a radiation source connected to the C-arm and emitting radiation to a target blood vessel located on a table; and a processor for computing a target distance from the radiation source to the target blood vessel, on the basis of a first vertical distance from the isocenter to the table and a second vertical distance from the target blood vessel to the table, and computing a physical distance of the target blood vessel by using the computed target distance, from a blood vessel image obtained using radiation.

20 Claims, 9 Drawing Sheets

(56) References Cited

U.S. PATENT DOCUMENTS

| | | | |
|---|---|---|---|
| 10,068,320 | B2 | 9/2018 | Sakaguchi et al. |
| 10,470,730 | B2 | 11/2019 | Benishti et al. |
| 11,596,374 | B2 | 3/2023 | Ohashi et al. |
| 2007/0239395 | A1* | 10/2007 | Jenkins .......... A61B 6/583 702/158 |
| 2015/0093003 | A1 | 4/2015 | Goto et al. |
| 2015/0216621 | A1 | 8/2015 | Fichtinger et al. |
| 2017/0225015 | A1 | 8/2017 | Thieme et al. |
| 2020/0093447 | A1* | 3/2020 | Ruijters .......... A61B 6/032 |
| 2022/0164950 | A1* | 5/2022 | Aben .......... A61B 6/481 |

FOREIGN PATENT DOCUMENTS

| | | |
|---|---|---|
| KR | 2013-0057991 A | 6/2013 |
| KR | 10-2016-0103482 A | 9/2016 |
| KR | 2017-0088742 A | 8/2017 |
| KR | 2019-0003388 A | 1/2019 |
| KR | 102004642 B1 | 7/2019 |
| WO | 2012-008706 A2 | 1/2012 |

OTHER PUBLICATIONS

Keane et al., "In Vivo Validation of an Experimental Adaptive Quantitative Coronary Angiography Algorithm to Circumvent Overestimation of Small Luminal Diameters" Catheterization and cardiovascular diagnosis, 36(1), 17-24; discussion 25-6.1995.

Reiber et al., (1985) "Assessment of Dimensions and Image Quality of Coronary Contrast Catheters from Cineangiograms". Catheterization and Cardiovascular Diagnosis, 11(5), 521-531.

Fortin et al., "Pitfalls in the Determination of Absolute Dimensions Using Angiographic Catheters as Calibration Devices in Quantitative Angiography" Am J Cardiol 68:1176-1182. 1991.

Herman et al., (1994) "Radiological Quality of Coronary Guiding Catheters: A Quantitative Analysis" Catheterization and Cardiovascular Diagnosis, 33(1), 55-60.

Siemens Healthcare. (n.d.). Artis zee/zeego Operator Manual VD11 and higher (p. 566). Retrieved from http://www.siemens.com/healthcare.

DICOM Standards Committee. (2023). DICOM PS3.3 2023a—Information Object Definitions: XA Positioner Module. Retrieved from http://dicom.nema.org/medical/dicom/current/output/html/part03.html#chapter_C.

Al-Janabi et al., "Coronary artery height differences and their effect on fractional flow reserve," Cardiol J, vol. 28, No. 1, pp. 41-48, 2021, doi: 10.5603/CJ.a2019.0031.

Sachdev et al., "Topic Review Cardiofel Newslet Nov. 2018; 1(5): 27-38 Coronary Angiography Basic Views." [Online]. Available: https://cardiofellows.com/newsletter-november-2018.html.

Blum (1967). "A Transformation for Extracting New Descriptorsof Shape", In Wathen-Dunn, Weiant (ed.). Models for the Perception of Speech and Visual Form. Cambridge, Massachusetts: MIT Press. pp. 362-380.

DICOM PS3.3 2023a—Information Object Definitions, C.8.19.6.9.1 XRay Projection Pixel Calibration Macro, available at https://dicom.nema.org/medical/Dicom/2017c/output/chtml/part03/sect_C.8.19.6.9.html Accessed on Feb. 27, 2023.

* cited by examiner

BLOOD VESSEL IMAGE CALIBRATION METHOD AND DEVICE

CROSS-REFERENCES TO RELATED APPLICATIONS

This application is a U.S. national phase application, pursuant to 35 U.S.C. § 371, of International Patent Application No. PCT/KR2023/005946, filed on May 2, 2023, which is based upon and claims the benefit of priority to Korean Patent Application Nos. 10-2022-0054209, filed on May 2, 2022, and 10-2023-0056529, filed on Apr. 28, 2023. The disclosures of the above-listed applications are hereby incorporated by reference herein in their entirety.

TECHNICAL FIELD

The following disclosure relates to a blood vessel image calibration method.

BACKGROUND ART

Angiography is a diagnostic procedure that visualizes blood vessels and their conditions using X-rays, and is a useful tool for examining vascular diseases. In angiography, which is useful for diagnosing vascular diseases, accurately measuring blood vessel size is important for determining the severity of the disease and an appropriate treatment method. For this purpose, a quantitative coronary analysis (QCA) method, which accurately measures blood vessel size, may be used. The QCA method is important for the diagnosis and treatment of coronary artery diseases. When using the QCA method, the discrepancy between the size of a blood vessel depicted in an image and the actual size of the blood vessel and the inaccurate assessment of the blood vessel size may cause errors in the diagnosis and treatment of vascular diseases. To solve these issues, various calibration methods, including catheter calibration and automatic calibration, are proposed. However, catheter calibration may have an issue that the accuracy of blood vessel diameter measurement may be affected when an angiographic catheter is used as a scaling device for a QCA system, and an issue that changes in catheter configuration may result in differences in contour detection due to different levels of X-ray attenuation, which may lead to inaccurate measurement results. Automatic calibration may have an issue in that it may be performed only when an object is exactly located at the isocenter.

DISCLOSURE OF THE INVENTION

Technical Solutions

A blood vessel image processing method, performed by a processor, according to an embodiment may include emitting radiation to a target blood vessel located on a table using a radiation source connected to a C-arm, computing a target distance from the radiation source to the target blood vessel, based on a first vertical distance from an isocenter of the C-arm to the table and a second vertical distance from the target blood vessel to the table, and computing a physical distance of the target blood vessel using the computed target distance from a blood vessel image captured using the radiation.

The isocenter may be a center of a rotation trajectory of the radiation source generated in response to a rotation of the C-arm.

The emitting of the radiation to the target blood vessel may include moving the table for the radiation source, the target blood vessel, and the isocenter to be disposed in one straight line.

The emitting of the radiation to the target blood vessel may include moving the table together for the radiation source, the target blood vessel, and the isocenter to be disposed in one straight line, in response to a position of the radiation source changing in response to the rotation of the C-arm.

The computing of the target distance may include computing the target distance based on the first vertical distance, the second vertical distance, and a projection angle of the radiation.

The projection angle of the radiation may be an angle between an axis orthogonal to a plane including a surface of the table and an axis corresponding to a projection direction of the radiation.

The computing of the target distance may include computing a first value by subtracting the second vertical distance from the first vertical distance, computing a second value by dividing the computed first value by a cosine value of the projection angle of the radiation, and computing the target distance as a value obtained by subtracting the computed second value from a straight line distance from the radiation source to the isocenter.

The radiation source may rotate based on at least one of a first rotation axis parallel to the table plane while including the isocenter or a second rotation axis different from the first rotation axis, based on the rotation of the C-arm.

The computing of the physical distance of the target blood vessel may include computing a calibration factor based on the computed target distance.

The computing of the calibration factor may include computing the calibration factor as a value computed by multiplying, by an imager pixel spacing, a value computed by dividing the computed target distance by a distance from the radiation source to an image receptor.

The computing of the physical distance of the target blood vessel may include computing a physical distance corresponding to a diameter of the target blood vessel, by multiplying the computed calibration factor by a number of pixels corresponding to the diameter of the target blood vessel shown in the captured blood vessel image.

An electronic device for processing a blood vessel image according to an embodiment may include a C-arm having an arc shape open toward an isocenter, a radiation source connected to the C-arm to emit radiation to a target blood vessel located on a table, and a processor configured to compute a target distance from the radiation source to the target blood vessel, based on a first vertical distance from the isocenter to the table and a second vertical distance from the target blood vessel to the table, and compute a physical distance of the target blood vessel using the computed target distance from a blood vessel image captured using the radiation.

Effects of the Invention

A method of processing a blood vessel image according to an embodiment may compute a calibration factor at a high accuracy by computing the distance from a radiation source to an object, and may provide accurate blood vessel size information of a target blood vessel from a blood vessel image acquired by capturing the target blood vessel based on the computation of the calibration factor at a high accuracy.

A method of processing a blood vessel image according to an embodiment may greatly help diagnose and treat vascular diseases by providing accurate blood vessel size information of a target blood vessel, and furthermore, may contribute to the development of diagnosis and treatment of new vascular diseases.

A method of processing a blood vessel image according to an embodiment may compute a calibration factor at a high accuracy, thereby reducing the deviation between result values for blood vessel size information of a target blood vessel of electronic devices even when blood vessel images are captured using various types of electronic devices.

BEST MODE FOR CARRYING OUT THE INVENTION

Figure 1:
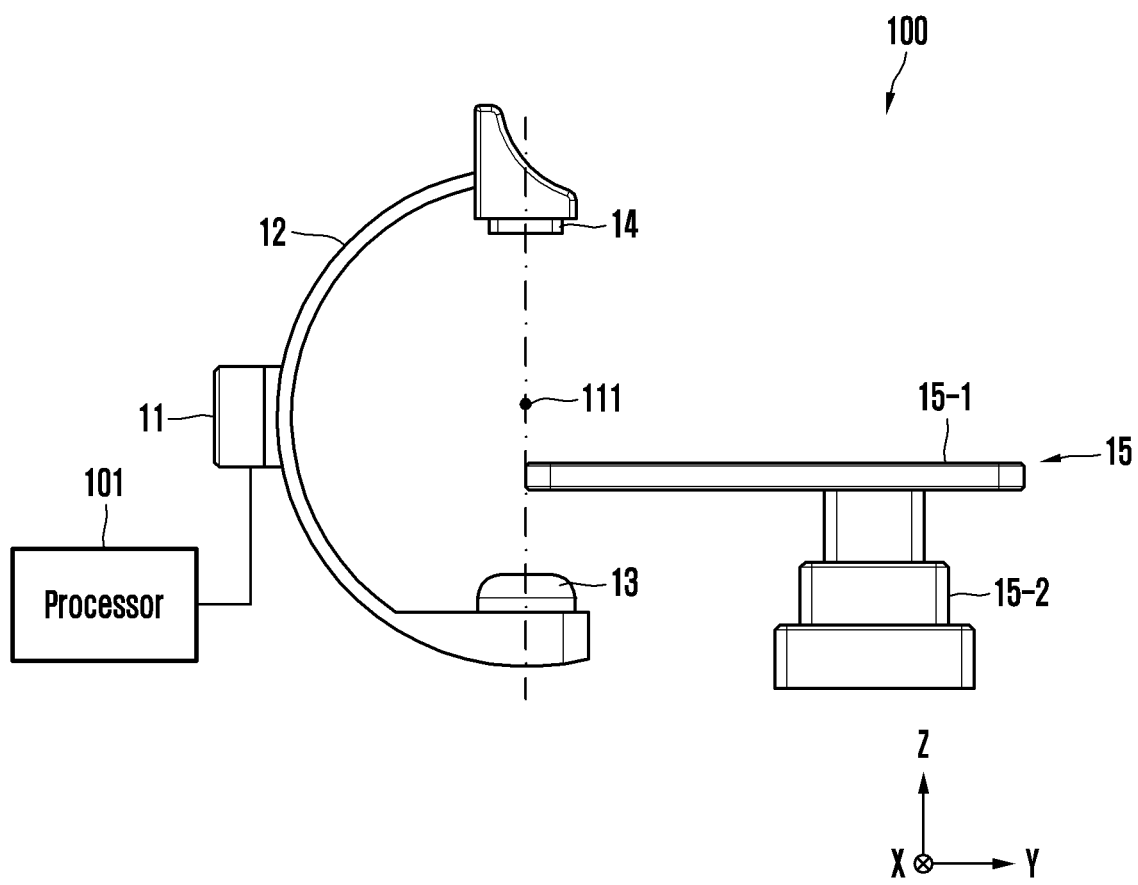
FIG. 1 is a diagram illustrating the structure of a medical electronic device according to an embodiment.

The following detailed structural or functional description is provided as an example only and various alterations and modifications may be made to the embodiments. Here, the embodiments are not construed as limited to the disclosure and should be understood to include all changes, equivalents, and replacements within the idea and the technical scope of the disclosure.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms used herein including technical or scientific terms have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, embodiments will be described in detail with reference to the accompanying drawings. When describing the embodiments with reference to the accompanying drawings, like reference numerals refer to like components, and any repeated description related thereto will be omitted.

FIG. 1 is a diagram illustrating the structure of a medical electronic device according to an embodiment.

A medical electronic device 100 (hereinafter, the "electronic device") according to an embodiment may be a device for capturing a blood vessel image by emitting radiation to blood vessels of a subject. The types of blood vessels may include, for example, the left main coronary artery (LM), the left anterior descending artery (LAD), the left circumflex artery (LCX), and the right coronary artery (RCA). The electronic device 100 may capture blood vessels using coronary angiography.

In an embodiment, the electronic device 100 may include a body portion 11, a C-arm 12, a radiation emitter 13, and a radiation detector 14. The electronic device 100 may further include a table 15 to place a subject on and a processor 101 to process blood vessel images.

The C-arm 12 may have a curved C-shaped arc shape with one open side. For example, when the C-arm 12 is vertically erected based on the floor on which the electronic device 100 is placed, the C-arm 12 may have a symmetrical shape based on a plane including an isocenter 111 and being parallel to the floor. The isocenter 111 may be a portion or point that is the center of a flux of radiation emitted from multiple positions irrespective of a rotation of the C-arm, and may be defined as a point where a first rotation axis and a second rotation axis of the C-arm intersect. The isocenter 111 may be the center of a rotation trajectory of the radiation emitter 13 (or a radiation source (not shown)) generated in response to a rotation of the C-arm 12. The C-arm 12 may have a shape open toward the isocenter 111.

The body portion 11 may be connected to the C-arm 12. The body portion 11 may be mechanically coupled with the C-arm 12. The C-arm 12 may rotate based on the body portion 11. The C-arm 12 may rotate within a y-z plane based on the body portion 11. For example, a protrusion included in the body portion 11 and a moving guide included in the C-arm 12 may be coupled to each other, and the C-arm 12 may rotate within the y-z plane along the moving guide based on a rotation axis that is parallel to the x-axis and passes through the isocenter 111. Further, the C-arm 12 may also rotate within an X-Z plane based on the body portion 11. For example, in a state in which the point where the body portion 11 and the C-arm 12 meet is fixed, the C-arm 12 may rotate within the X-Z plane based on a rotation axis that is parallel to the y-axis and passes through the isocenter 111.

The electronic device 100 may include the radiation emitter 13 and the radiation detector 14 that are disposed to face each other with the isocenter 111 interposed therebetween on an inner side surface of the C-arm 12. Each of the radiation emitter 13 and the radiation detector 14 may be connected to the C-arm 12. The radiation emitter 13 may include at least one radiation source, and emit radiation toward a subject using the at least one radiation source. The radiation detector 14 may include a radiation detection sensor, and detect radiation transmitted through the blood vessels of the subject after emitted from the radiation emitter 13 using the radiation detection sensor.

A subject may be laid down on the table 15. More specifically, the table 15 may include a table top 15-1 on which a subject is to be laid down and a table support 15-2 supporting the table top 15-1. The table support 15-2 may be anchored to the floor. For example, the table top 15-1 은 may be movably coupled to the table support 15-2. The electronic device 100 may further include an actuator (not shown) to change the position of the table top 15-1 based on the table support 15-2. The electronic device 100 may move the table top 15-1 based on the table support 15-2 using the actuator (not shown). The actuator (not shown) may include a motor (e.g., an electric motor) and a power transmission structure.

The table top 15-1 may move laterally and vertically based on the table support 15-2. For example, the electronic device 100 may move the table top 15-1 laterally on a plane (e.g., the X-Y plane) that is parallel to the surface of the table. The surface of the table may be the top surface of the table top 15-1. The electronic device 100 may move the table top 15-1 vertically on an axis (e.g., the Z-axis) that is perpendicular to the plane (e.g., the X-Y plane) that is parallel to the surface of the table. In the following description, moving the table 15 may refer to moving the table top 15-1 based on the table support 15-2. For example, the electronic device 100 may move the table 15 to accurately emit radiation to a target blood vessel of the subject.

The electronic device 100 may control the C-arm 12 so that the C-arm 12 may rotate around the subject placed on the table 15. The electronic device 100 may fix the C-arm 12 and then emit radiation to the target blood vessel of the subject on the table 15 using the radiation source in the radiation emitter 13 connected to the C-arm 12. The radiation emitted to the blood vessels of the subject may be X-rays.

Figure 2:
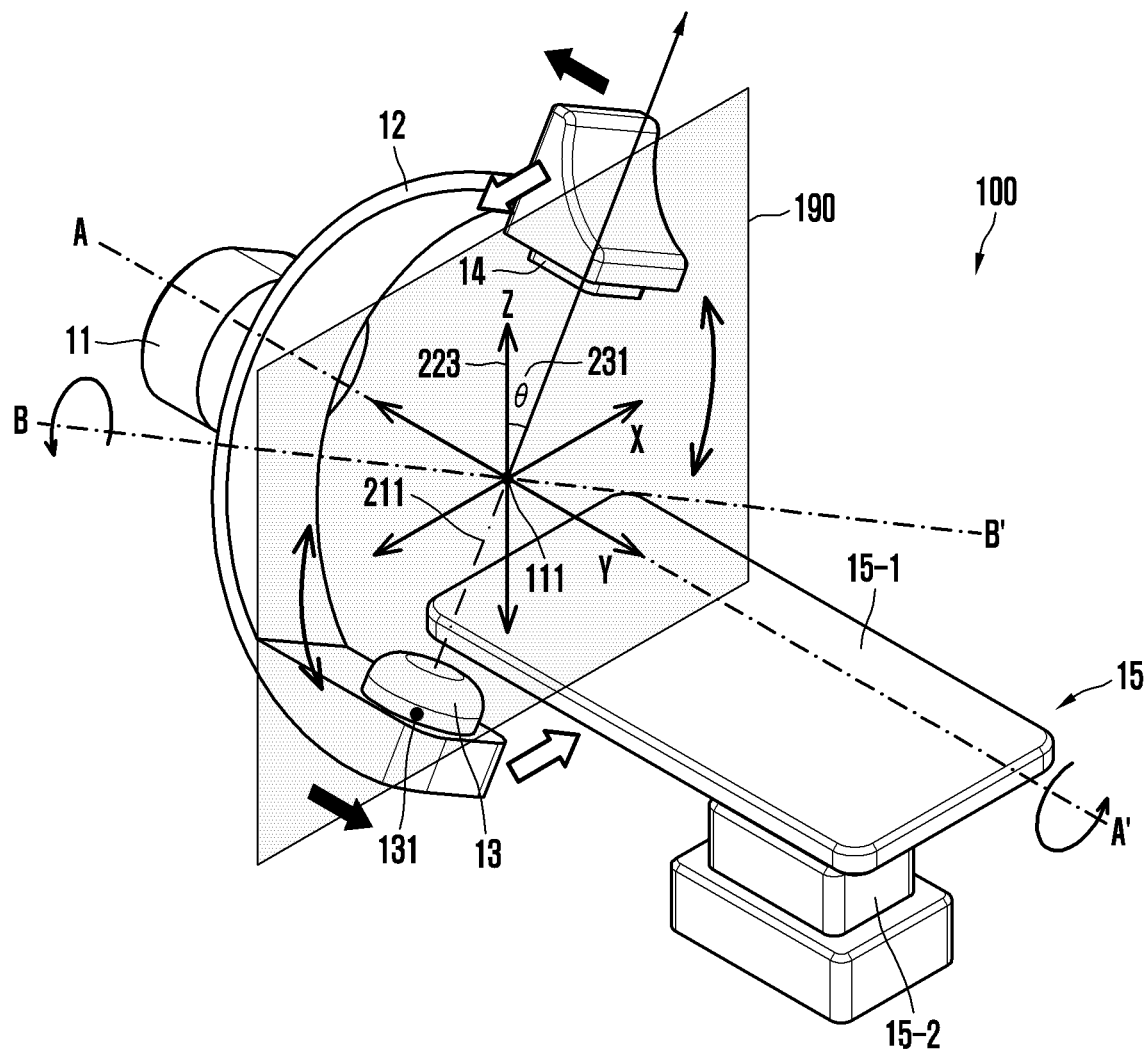
FIG. 2 is a diagram illustrating a change in the projection angle of radiation in response to a rotation of a C-arm included in an electronic device according to an embodiment.

FIG. 2 is a diagram illustrating a change in the projection angle of radiation in response to a rotation of a C-arm included in an electronic device according to an embodiment.

In an embodiment, the electronic device 100 may emit radiation to a target blood vessel of a subject placed on the table 15 using a radiation source 131 included in the radiation emitter 13.

The electronic device 100 according to an embodiment may rotate the radiation source based on at least one of a first rotation axis A-A' parallel to the table plane while including the isocenter 111 and a second rotation axis B-B' different from the first rotation axis A-A', based on a rotation of the C-arm. For example, the radiation source may rotate on one of a plane perpendicular to the first rotation axis A-A' parallel to the table plane while including the isocenter 111 or a plane perpendicular to the second rotation axis B-B' different from the first rotation axis A-A' while including the isocenter 111. The second rotation axis B-B' and the first rotation axis A-A' may intersect, and may be orthogonal to each other, for example, at the isocenter 111. For reference, for ease of description, an example in which the C-arm and the radiation source rotate on one plane is described, but embodiments are not limited thereto, and the C-arm and the radiation source may rotate simultaneously based on two rotation axes A-A' and B-B'.

For example, the electronic device 100 may rotate the C-arm 12 with respect to the body portion 11 about the first rotation axis A-A'. The first rotation axis A-A' may be an axis connecting the point where the C-arm 12 and the body portion 11 are coupled and the isocenter 111. The position of the radiation source 131 may change in response to the rotation of the C-arm 12. For example, in response to the rotation of the C-arm 12 about the first rotation axis A-A', the radiation source 131 may rotate forming a rotation trajectory on a plane 190 perpendicular to the first rotation axis A-A' while including the isocenter 111. FIG. 2 exemplarily shows the X-Z plane as the plane 190 perpendicular to the first rotation axis A-A'.

The radiation source 131 may rotate forming a rotation trajectory in a shape similar to a circle on the plane 190 in response to a rotation of the C-arm 12. The rotation trajectory along which the radiation source 131 moves when the C-arm 12 rotates may not be geometrically a true circle and may be a circle partially distorted due to sagging or vibration of the C-arm 12.

Further, the electronic device 100 may rotate the C-arm 12 with respect to the body portion 11 about the second rotation axis B-B'. The second rotation axis B-B' may be an axis intersecting with (e.g., orthogonal to) the first rotation axis A-A' while passing through the isocenter 111. For example, in response to the rotation of the C-arm 12 about the second rotation axis B-B', the radiation source 131 may rotate forming a rotation trajectory on a plane perpendicular to the second rotation axis B-B' while including the isocenter 111. For reference, FIG. 2 shows an example in which the second rotation axis B-B' rotates together as the C-arm rotates based on the first rotation axis A-A'. However, if the C-arm 12 rotates based on the second rotation axis B-B' while the radiation source 131 and the radiation detector 14 are on the Z-axis, the second rotation axis B-B' may be parallel to the X-axis, and the radiation source 131 may rotate forming a rotation trajectory on the Y-Z plane.

If the position of the radiation source 131 changes in response to a rotation of the C-arm 12, a projection angle θ 231 of the radiation emitted from the radiation source 131 may change. In other words, in response to a rotation of the C-arm 12, the projection angle θ 231 of the radiation emitted from the radiation source may change.

The projection angle 231 of the radiation may be the angle between an axis (e.g., the Z-axis) orthogonal to a plane including the surface of the table 15 and an axis 211 corresponding to the projection direction (irradiation direction) of the radiation emitted from the radiation source 131. The projection direction of the radiation may be a direction from the radiation emitter 13 (or the radiation source 131) toward the radiation detector 14 (or the radiation detection sensor). The axis 211 corresponding to the projection direction of the radiation may be an axis connecting the radiation emitter 13 and the radiation detector 14. The projection angle 231 of the radiation may be an angle between −180 degrees and 180 degrees.

The isocenter 111 may be defined in various manners based on a rotation of the C-arm 12. For example, the isocenter 111 may be a point where radiation emitted from various positions of the radiation source in response to a rotation of the C-arm 12 intensively congregates. As another example, the isocenter 111 may be the geometric center of a rotation trajectory of the radiation source 131. As another example, the isocenter 111 may be the center of rotation of the C-arm 12.

Figure 3:
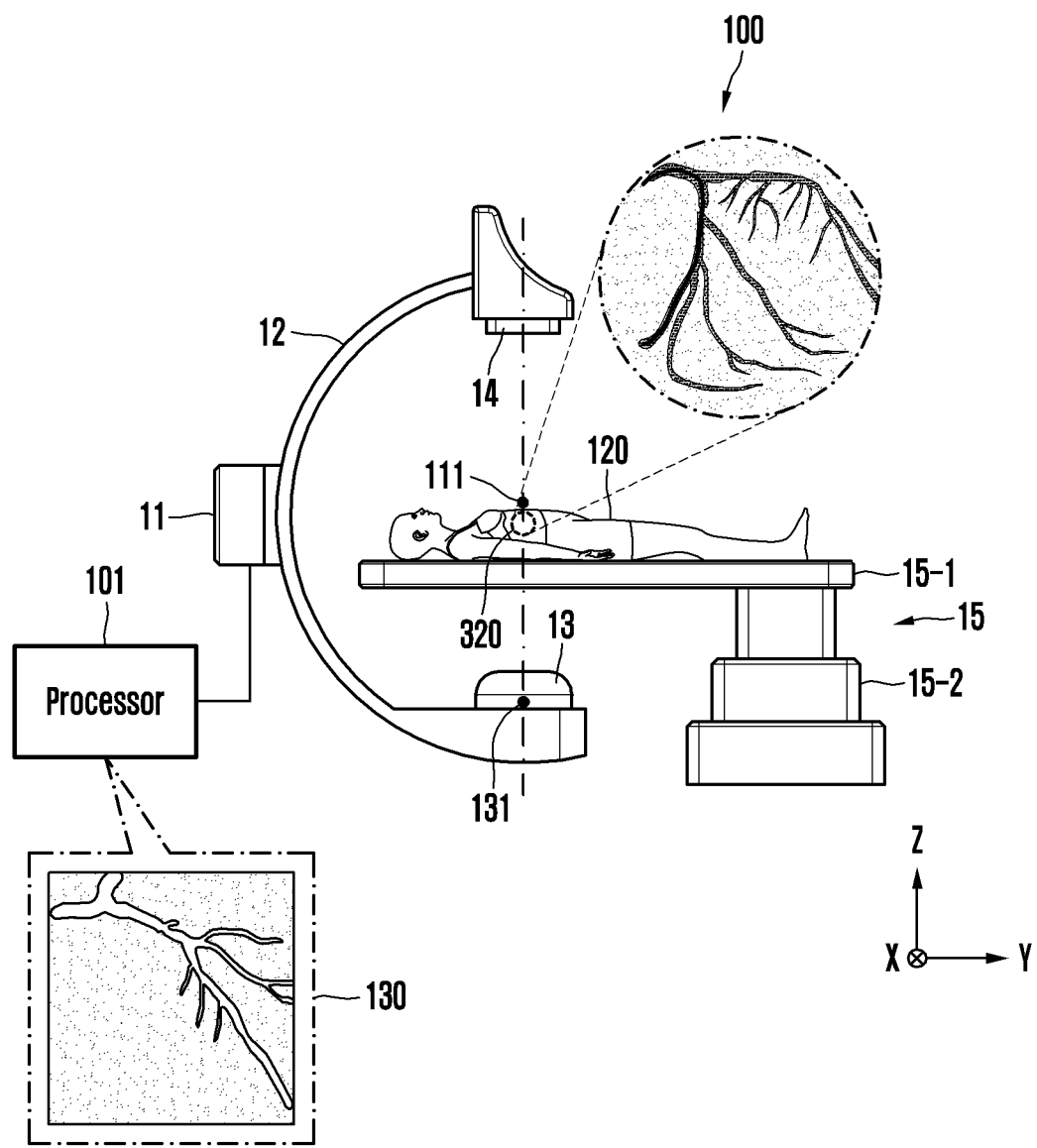
FIG. 3 is a diagram illustrating a process of computing a physical distance of a target blood vessel from a blood vessel image by an electronic device according to an embodiment.

FIG. 3 is a diagram illustrating a process of computing a physical distance of a target blood vessel from a blood vessel image by an electronic device according to an embodiment.

In an embodiment, a subject 120 may be placed on the table top 15-1 of the electronic device 100. The electronic device 100 may generate a blood vessel image 130 acquired by capturing a target blood vessel 320 of the subject 120 using radiation emitted from the radiation source 131.

The processor 101 of the electronic device 100 may derive a quantitative analysis result such as the diameter of the target blood vessel 320 or the length of a lesion from the generated blood vessel image 130. To derive a quantitative analysis result related to the target blood vessel 320 from the blood vessel image 130, the processor 101 may need to convert a distance measured in the blood vessel image 130 into a real-world physical distance in micrometers (μm), millimeters (mm), or centimeters (cm). Accordingly, the processor 101 may convert the distance measured in the blood vessel image 130 into a physical distance using a calibration factor.

In detail, the physical distance may be computed by multiplying the calibration factor by the number of pixels corresponding to the distance measured in the blood vessel image 130. For example, the physical distance may be expressed as in Equation 1 below.

$$\text{Physical distance} = \text{Calibration factor} \times \text{Number of pixels} \quad \text{[Equation 1]}$$

Referring to Equation 1, the calibration factor may be a physical distance corresponding to the length (e.g., the horizontal length or vertical length) of one pixel in the blood vessel image 130. To accurately compute the physical distance, the calibration factor needs to be computed accurately.

The calibration factor may represent the spatial relationship between an object in a blood vessel image and an object in the real world. The calibration factor may be computed by multiplying, by an imager pixel spacing, a value computed by dividing the distance from the radiation source to a target object (a source-to-object distance (SOD)) by the distance from the radiation source to an image receptor (a source-to-image receptor distance (SID)). The imager pixel spacing may be the length (e.g., the horizontal length or vertical length) of one pixel in the blood vessel image. That is, the calibration factor may be expressed as in Equation 2 below.

$$\text{Calibration factor} = \frac{SOD}{SID} \times \text{Imager pixel spacing} \quad \text{[Equation 2]}$$

In Equation 2, SOD may denote the straight line distance from a source (e.g., the radiation source) to an object to be captured, and SID may denote the straight line distance from the source to the image receptor. The distance from the source to the image receptor (SID) and the imager pixel spacing may be extracted from metadata of Digital Imaging and Communications in Medicine (DICOM). DICOM may be a standard for storing and transmitting data related to images generated by medical electronic devices. After all, referring to Equation 2, accurately computing the calibration factor requires accurately measuring the straight line distance from the source to the object to be captured (SOD). In the past, medical electronic devices computed the SOD by approximating the distance from the radiation source 131 to the target blood vessel 320 to the distance from the radiation source 131 to the isocenter 111, and such approximation caused an issue of inaccurate computation of a calibration factor. In contrast, in an embodiment, the electronic device 100 may accurately compute the SOD without approximating the straight line distance from the radiation source 131 to the target blood vessel 320, thereby computing the calibration factor more accurately than the conventional method. Hereinafter, a method of measuring the straight line distance from the radiation source 131 to the target blood vessel 320 is described in detail.

In an embodiment, the electronic device 100 may emit radiation to the target blood vessel 320 of the subject 120 placed on the table top 15-1 using the radiation source 131 included in the radiation emitter 13. The electronic device 100 may compute a target distance from the radiation source 131 to the target blood vessel 320 based on a first vertical distance from the isocenter 111 to the table 15 and a second vertical distance from the target blood vessel 320 to the table 15. Here, the first vertical distance from the isocenter 111 to the table 15 may be the vertical distance from the isocenter 111 to the top surface of the table top 15-1. Similarly, the second vertical distance from the target blood vessel 320 to the table 15 may be the vertical distance from the target blood vessel 320 to the top surface of the table top 15-1.

More specifically, the electronic device 100 may adjust the position of the target blood vessel 320 through the table 15, before emitting radiation to the target blood vessel 320 using the radiation source 131. The electronic device 100 may move the table 15 for the radiation source 131, the target blood vessel 320, and the isocenter 111 to be disposed in one straight line. In an embodiment, the electronic device 100 may cause the radiation source 131, the target blood vessel 320, and the isocenter 111 to be disposed in one straight line by moving the table top 15-1 only laterally on the X-Y plane. In another embodiment, the electronic device 100 may cause the radiation source 131, the target blood vessel 320, and the isocenter 111 to be disposed in one straight line by moving the table top 15-1 both laterally on the X-Y plane and vertically on the Z-axis.

In an embodiment, if the position of the radiation source 131 changes in response to a rotation of the C-arm 12, the table top 15-1 may be moved together for the radiation source 131, the target blood vessel 320, and the isocenter 111 to be disposed in one straight line.

In an embodiment, the electronic device 100 may dispose the isocenter 111 on the same straight line as the radiation source 13 and the target blood vessel 320 by moving the table 15 laterally on a plane including the surface of the table. The height of the table 15 may be fixed, but is not limited thereto, and may be variable. For example, the electronic device 100 may compute the height of the target blood vessel 320 from the floor. The electronic device 100 may compute the height of the target blood vessel 320 from the floor by summing the height of the target blood vessel 320 from the surface of the table and the height of the table 320 from the floor. However, embodiments are not limited thereto, and the electronic device 100 may obtain the height from the table 320 (e.g., the surface of the table) to the target blood vessel 320. The electronic device 100 may generate a plane including a point corresponding to the target blood vessel 320 while being parallel to the floor (or the X-Y plane) based on the position (e.g., the height) of the target blood vessel 320. The electronic device 100 may compute a point where the plane including the target blood vessel 320 while being parallel to the floor intersects a straight line axis connecting the radiation source 131 and the isocenter 111 ("the intersection point"). The electronic device may move the table top 15-1 laterally on the X-Y plane so that the target blood vessel 320 may be placed at the computed intersection point.

In an embodiment, the electronic device 100 may compute a target distance indicating the straight line distance from the radiation source 131 to the target blood vessel 320 using a plurality of parameters, after adjusting the position of the target blood vessel 320 by moving the tabletop 15-1. The plurality of parameters may include, for example, the position of the table 15, the position of the target blood vessel 320, and the projection angle (irradiation angle) of radiation emitted from the radiation source 131 (e.g., the projection angle 231 of the radiation of FIG. 2). More specifically, the electronic device 100 may accurately compute the target distance from the radiation source 131 to the target blood vessel 320 based on the first vertical distance from the isocenter 111 to the table 15, the second vertical distance from the target blood vessel 320 to the table 15, and the projection angle of the radiation emitted from the radiation source 131.

Figure 4:
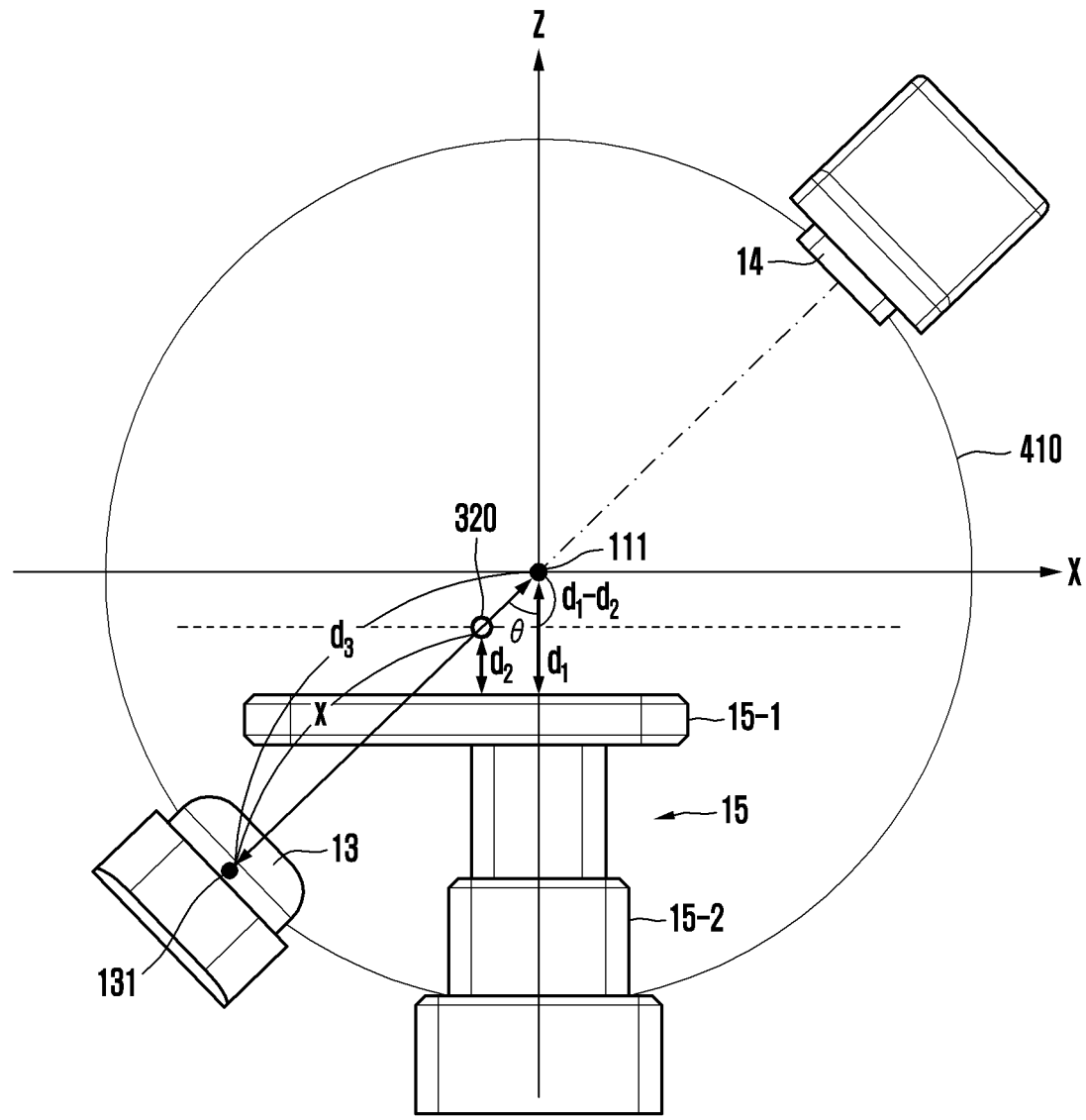
FIG. 4 is a diagram illustrating a process of computing a straight line distance from a radiation source to a target blood vessel by an electronic device according to an embodiment.

FIG. 4 is a diagram illustrating a process of computing a straight line distance from a radiation source to a target blood vessel by an electronic device according to an embodiment.

FIG. 4 is a side view of an electronic device (e.g., the electronic device 100 of FIG. 1) from the X-Z plane. The electronic device may align the radiation source 131, the target blood vessel 320, and the isocenter 111 in a straight line by moving the table top 15-1, before emitting radiation to the target blood vessel 320 using the radiation source 131.

In an embodiment, the electronic device may compute a first value ($d_1 - d_2$) by subtracting a second vertical distance ($d_2$) from the target blood vessel 120 to the table 15 from a first vertical distance ($d_1$) from the isocenter 111 to the table 15. The first value ($d_1 - d_2$) may represent the vertical distance from the isocenter 111 to the target blood vessel 320. Then, the electronic device may compute a second value by dividing the computed first value ($d_1 - d_2$) by a cosine value ($\cos(\theta)$) of the projection angle of the radiation (e.g., the projection angle 231 of the radiation of FIG. 2). The second value $$\left(\frac{d_1 - d_2}{\cos \theta}\right)$$

may represent the straight line distance from the isocenter 111 to the target blood vessel 320. The electronic device may compute a target distance (x) from the radiation source 131 to the target blood vessel 320 as a value obtained by subtracting the computed second value (i.e., the straight line distance from the isocenter 111 to the target blood vessel 320) from a straight line distance ($d_3$) from the radiation source 131 to the isocenter 111.

In summary, the target distance from the radiation source 131 to the target blood vessel 320 may be computed as in Equation 3 below.

$$SOD = \text{Source to Isocenter} - \frac{\text{Isocenter to table} - \text{Object height}}{\cos \theta} \quad \text{[Equation 3]}$$

In Equation 3 above, SOD may denote the straight line distance from the radiation source 131 to the target blood vessel 320, Source to Isocenter may denote the straight line distance ($d_3$) from the radiation source 131 to the isocenter 111, Isocenter to table may denote the vertical distance ($d_1$) from the isocenter 111 to the table 15, Object height may denote the vertical distance ($d_2$) from the target blood vessel 320 to the table 15, and $\theta$ may denote the projection angle of the radiation.

In an embodiment, the electronic device may compute the target distance and then, compute a calibration factor based on the computed target distance. As described above, the electronic device may convert a distance in the blood vessel image 130 into a physical distance using the computed calibration factor. For example, the electronic device may compute a physical distance corresponding to the diameter of a target blood vessel by multiplying the calibration factor by the number of pixels corresponding to the diameter of the target blood vessel shown in the captured blood vessel image. As another example, the electronic device may compute a physical distance corresponding to the length of a lesion shown in the blood vessel image by multiplying the calibration factor by the number of pixels corresponding to the length of the lesion shown in the captured blood vessel image. In addition, the electronic device may derive various quantitative analysis results related to the target blood vessel in the blood vessel image (e.g., the blood vessel image 130 of FIG. 3) using the computed calibration factor.

Figure 5:
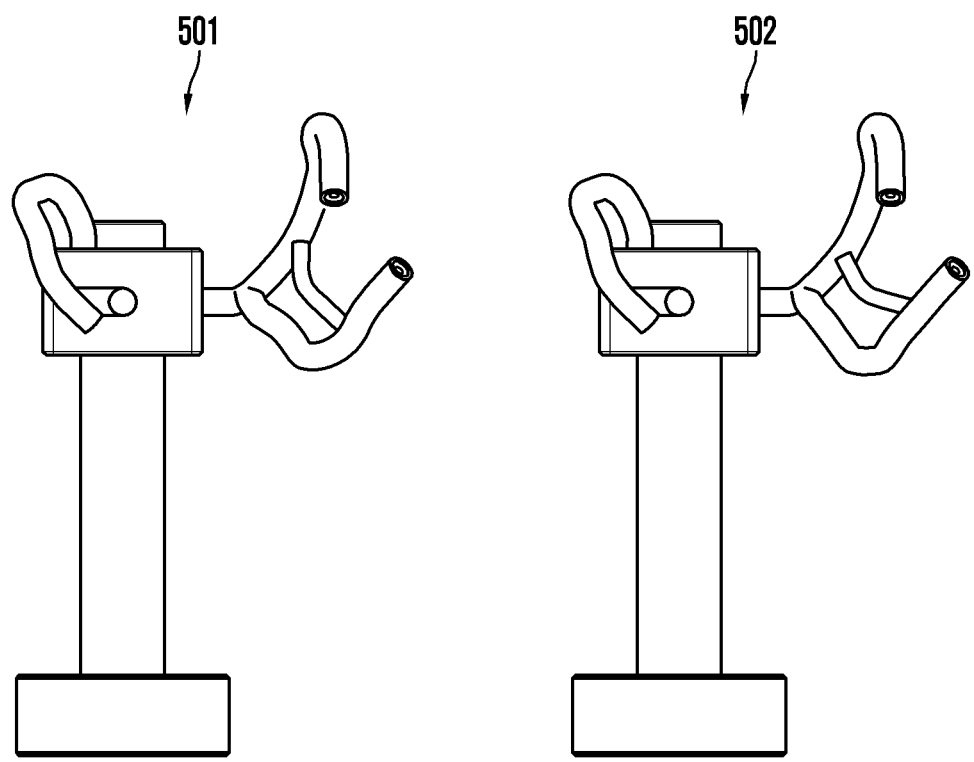
FIG. 5 illustrates vessels designed using CT data sets of a subject for a phantom experiment.

FIG. 5 illustrates vessels designed using CT data sets of a subject for a phantom experiment.

An electronic device according to an embodiment may compute a target distance from a radiation source to a target blood vessel based on a first vertical distance from an isocenter to a table and a second vertical distance from the target blood vessel to the table, and compute a calibration factor based on the computed target distance. Hereinafter, for ease of description, a method of computing a calibration factor based on a target distance from a radiation source to a target blood vessel is described as the method of computing a calibration factor according to the embodiment, and a method of computing a calibration factor by approximating the distance from a radiation source to a target blood vessel to the distance from the radiation source to an isocenter is described as the method of computing a calibration factor according to the comparative embodiment.

A phantom experiment was carried out to verify the accuracy of the method of computing a calibration factor according to the embodiment. The phantom experiment used four coronary phantoms with diameters of 2.5 mm, 3.0 mm, 3.5 mm, and 4.0 mm, respectively, using CT datasets of a subject. The error range of the inner diameter was verified to be approximately 0.1 mm. The generated coronary artery may be filled with a contrast agent so as to be detectable by radiation. Further, to reproduce the height of the actual blood vessels, the coronary artery may be placed on a stand. FIG. 5 shows an example in which the generated left coronary artery (LCA) 501 is placed on a stand at a height of 150 mm and the generated right coronary artery (RCA) 502 is placed on a stand at a height of 175 mm.

In the phantom experiment, a plurality of blood vessel images may be acquired by performing angiography on the generated coronary arteries. For example, for the left coronary artery (LCA) 501, radiation may be emitted at a projection angle that causes the left coronary artery (LCA) 501 to include CAU, RAOCAU, RAOCRA, CRA, and LAOCRA, and for the right coronary artery (RCA) phantom 502, radiation may be emitted at a projection angle that causes the right coronary artery (RCA) 502 to include AP, LAO, and CRA. For reference, the height of the table may be changed considering the actual usage environment.

Figure 6A:
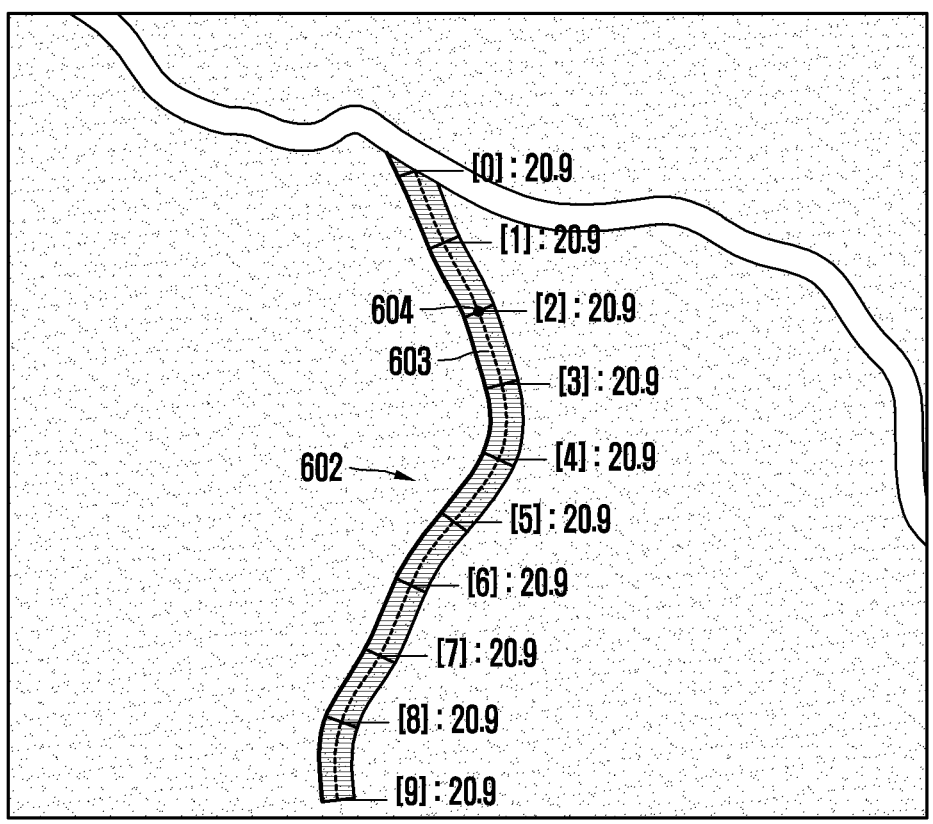
FIG. 6A is a diagram illustrating a blood vessel image labeled to estimate the diameter of a target blood vessel shown in the blood vessel image.

FIG. 6A is a diagram illustrating a blood vessel image labeled to estimate the diameter of a target blood vessel shown in the blood vessel image. For blood vessel images, the boundary of a target blood vessel 602 displayed in a corresponding blood vessel image may be labeled by a user (e.g., an expert). A total of 1920 images were acquired by performing phantom angiography using a commercial angiography device, and these images were acquired at generally used coronary angiography (CAG) routine radiation imaging angles (CAU, RAOCAU, RAOCRA, CRA and LAOCRA of LCA, and AP, LAO and CRA of RCA). In the captured 1920 images, a target blood vessel may be labeled by a professional labeler (e.g., a radiographer) with more than three years of experience, as shown in FIG. 6A.

Referring to FIG. 6A, the boundary of the target blood vessel 602 in a blood vessel image 601 may be labeled by the user, and after labeling, the diameter of the target blood vessel 602 may be estimated at each point included in a centerline 603 of the target blood vessel to measure the diameter of the target blood vessel 602. For example, at one point (e.g., a point 604) included in the centerline of the target blood vessel, a line segment perpendicular to the centerline 603 of the target blood vessel may be generated, the number of pixels (e.g., 20.9) corresponding to the diameter of the target blood vessel may be measured, and the diameter of the target blood vessel may be estimated by multiplying the measured number of pixels by a calibration factor.

Figure 6B:
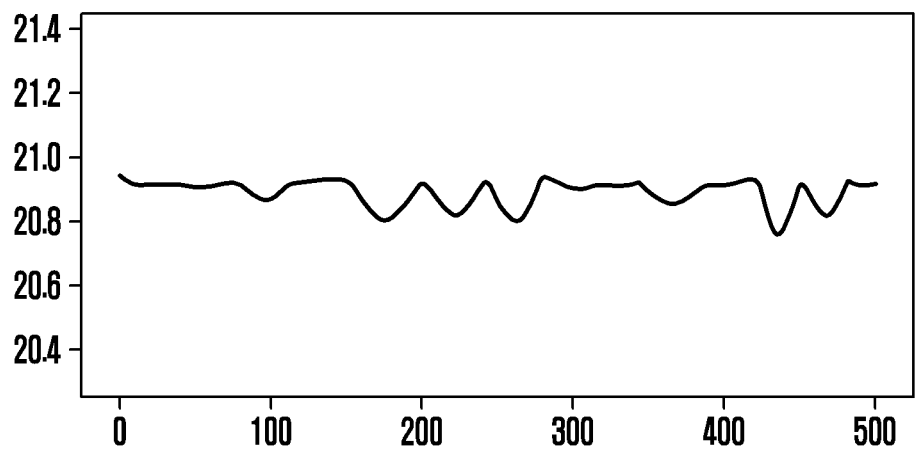
FIG. 6B illustrates graphs that estimate the diameter of a target blood vessel shown in a blood vessel image.
Figure 6B:
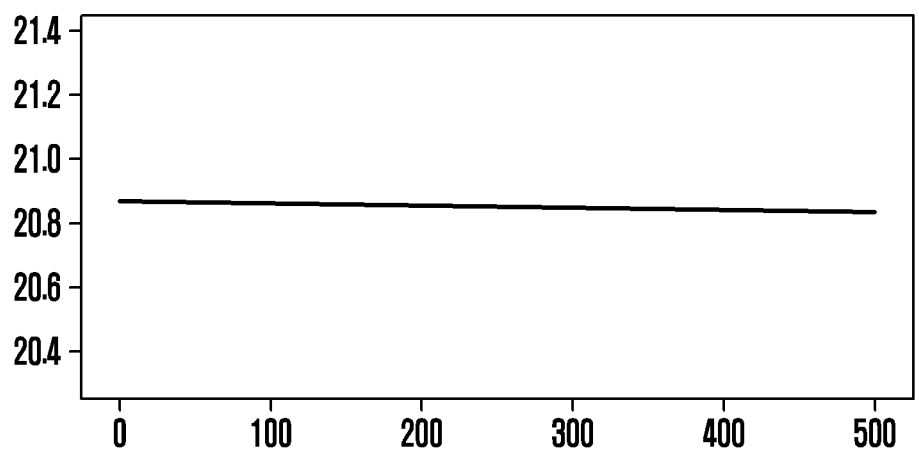

FIG. 6B illustrates graphs to estimate the diameter of a target blood vessel 602 shown in a blood vessel image. A graph 611 shows the diameters of the target blood vessel 602 estimated at the respective points while moving from the proximal part of the target blood vessel 602 to the distal part of the target blood vessel 602 along the centerline 603 of the target blood vessel. For example, the diameter of the blood vessel 602 may be measured as the number of pixels corresponding to the length (e.g., the diameter) from the boundary on one side (e.g., the left end) to the boundary on the other side (e.g., the right end) of the blood vessel on a normal line of the centerline. FIG. 6A shows an example in which 20.9 pixels are measured as the diameter of the blood vessel 602. In the graph 611, the x-axis may denote the distance one point is away from the proximal part of the target blood vessel along the centerline, and the y-axis may denote the number of pixels corresponding to the diameter of the target blood vessel measured in practice for the corresponding point. The graph 612 shows a trend line for the graph 611 using a linear regression analysis to reduce errors due to variability in measurement. Through the graph 612, the diameter of the target blood vessel 602 may be measured. In a phantom experiment, the accuracy of the method of computing a calibration factor according to the embodiment is evaluated by comparing the actual diameter of the target blood vessel and the estimated diameter of the target blood vessel.

Figure 7A:
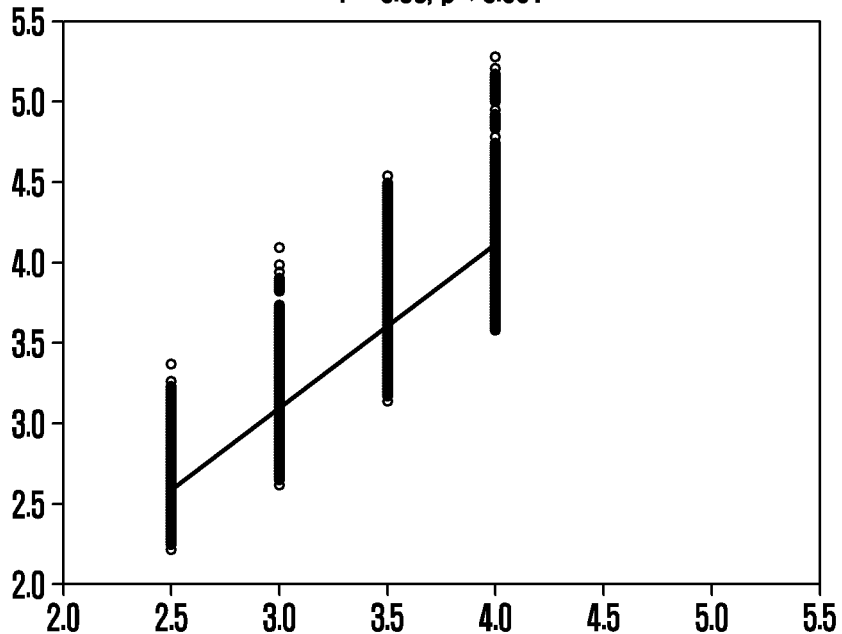
FIGS. 7A and 7B illustrate graphs for performance evaluation of a method of computing a calibration factor according to an embodiment and a method of computing a calibration factor according to a comparative embodiment.
Figure 7A:
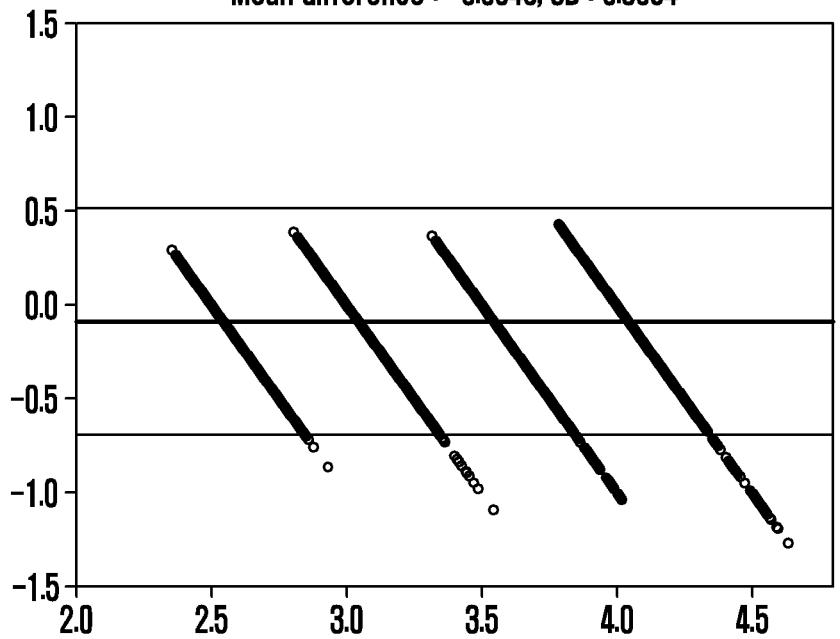
Figure 7B:
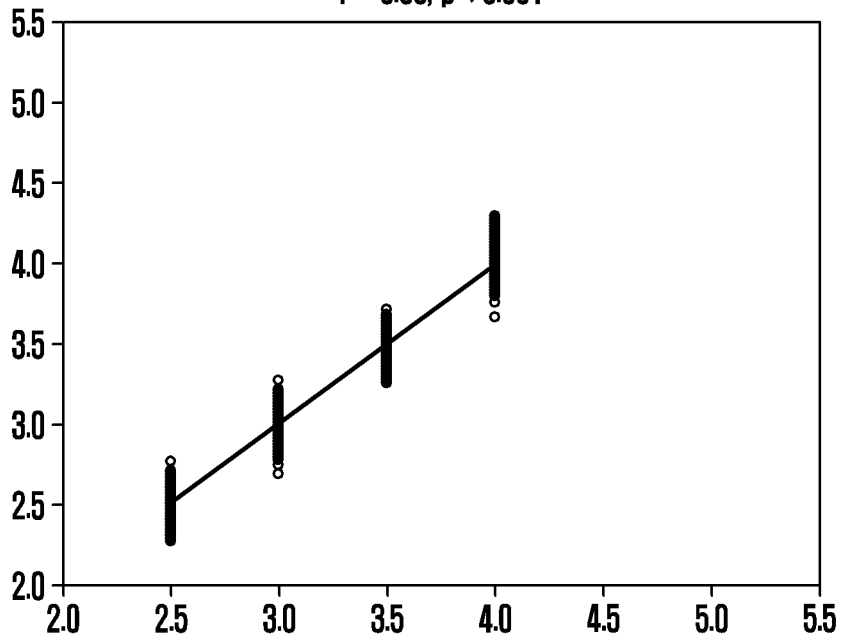
Figure 7B:
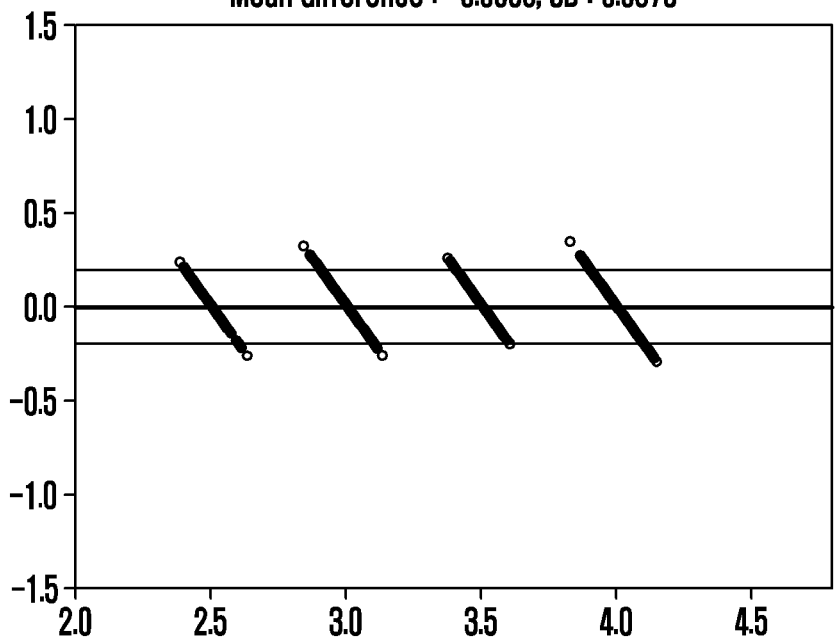

FIGS. 7A and 7B illustrate graphs for performance evaluation of the method of computing a calibration factor according to the embodiment and the method of computing a calibration factor according to the comparative embodiment. FIG. 7A shows the result when a conventional method (e.g., the conventional calibration method) is used, and FIG. 7B shows a comparison of the result derived by the newly developed above method.

FIG. 7A illustrates graphs showing the result of comparing the diameter of the target blood vessel estimated by the method of computing a calibration factor according to the comparative embodiment and the actual diameter of the target blood vessel.

In a graph 711, the true value of the diameter of the target blood vessel may be represented on the x-axis, and the value of the diameter of the target blood vessel estimated by the method of computing a calibration factor according to the comparative embodiment may be represented on the y-axis. Referring to the graph 711, in the method of computing a calibration factor according to the comparative embodiment, the Pearson correlation coefficient may be expressed as 0.8828 ($p<0.0001$). In a graph 712, the mean of the true value of the diameter of the target blood vessel and the value of the diameter of the target blood vessel estimated by the method of computing a calibration factor according to the comparative embodiment may be represented on the x-axis, and the difference between the true value of the diameter of the target blood vessel and the value of the diameter of the target blood vessel estimated by the method of computing a calibration factor according to the comparative embodiment may be represented on the y-axis. Referring to the graph 712, in the method of computing a calibration factor according to the comparative embodiment, the mean difference between the true value of the diameter of the target blood vessel and the value of the diameter of the target blood vessel estimated by the method of computing a calibration factor according to the comparative embodiment may be −0.0949 mm, and the limits of agreement may range from −0.6936 to 0.5037.

FIG. 7B illustrates graphs showing the result of comparing the diameter of the target blood vessel estimated by the method of computing a calibration factor according to the embodiment and the actual diameter of the target blood vessel. In a graph 721, the true value of the diameter of the target blood vessel may be represented on the x-axis, and the value of the diameter of the target blood vessel estimated by the method of computing a calibration factor according to the embodiment may be represented on the y-axis. Referring to the graph 721, in the method of computing a calibration factor according to the embodiment, the Pearson correlation coefficient may be expressed as 0.9880 ($p<0.0001$). In a graph 722, the mean of the true value of the diameter of the target blood vessel and the value of the diameter of the target blood vessel estimated by the method of computing a calibration factor according to the embodiment may be represented on the x-axis, and the difference between the true value of the diameter of the target blood vessel and the value of the diameter of the target blood vessel estimated by the method of computing a calibration factor according to the embodiment may be represented on the y-axis. Referring to the graph 722, in the method of computing a calibration factor according to the embodiment, the mean difference between the true value of the diameter of the target blood vessel and the value of the diameter of the target blood vessel estimated by the method of computing a calibration factor according to the embodiment may be 0.0007 mm, and the limits of agreement may range from −0.1705 to 0.1719.

It may be learned that the method of computing a calibration factor according to the embodiment is more excellent than the method of computing a calibration factor according to the comparative embodiment in terms of accuracy and precision of estimating the diameter of the target blood vessel. The method of computing a calibration factor according to the embodiment has a higher correlation coefficient and a narrower matching limit than the method of computing a calibration factor according to the comparative embodiment, which may indicate that the method of computing a calibration factor according to the embodiment provides a better match to the true value of the diameter of the target blood vessel.

The embodiments described herein may be implemented using a hardware component, a software component and/or a combination thereof. The devices, methods, and components described in the embodiments may be implemented using one or more general-purpose or special-purpose computers, such as, for example, a processor, a controller and an arithmetic logic unit (ALU), a digital signal processor (DSP), a microcomputer, a field-programmable gate array (FPGA), a programmable logic unit (PLU), a microprocessor or any other device capable of responding to and executing instructions in a defined manner. A processing device may run an operating system (OS) and one or more software applications that run on the OS. The processing device also may access, store, manipulate, process, and create data in response to execution of the software. For the purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described embodiments may be recorded in non-transitory computer-readable media including program instructions to implement various operations of the above-described embodiments. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described hardware devices may be configured to act as one or more software modules in order to perform the operations of the above-described examples, or vice versa.

A number of embodiments have been described above. Nevertheless, it should be understood that various modifications may be made to these embodiments. For example, suitable results may be achieved if the described techniques are performed in a different order, and/or if components in a described system, architecture, device, or circuit are combined in a different manner, and/or replaced or supplemented by other components or their equivalents.

Accordingly, other implementations, other embodiments, and equivalents to the claims are within the scope of the following claims.

The invention claimed is:

1. A blood vessel image processing method, performed by a processor, comprising:
    emitting radiation to a target blood vessel located on a table using a radiation source connected to a C-arm;
    computing a target distance from the radiation source to the target blood vessel, based on a first vertical distance from an isocenter of the C-arm to the table and a second vertical distance from the target blood vessel to the table; and
    computing a physical distance of the target blood vessel using the computed target distance from a blood vessel image captured using the radiation.

2. The blood vessel image processing method of claim 1, wherein
    the isocenter is a center of a rotation trajectory of the radiation source generated in response to a rotation of the C-arm.

3. The blood vessel image processing method of claim 1, wherein
    the emitting of the radiation to the target blood vessel comprises moving the table for the radiation source, the target blood vessel, and the isocenter to be disposed in one straight line.

4. The blood vessel image processing method of claim 3, wherein
    the emitting of the radiation to the target blood vessel comprises moving the table together for the radiation source, the target blood vessel, and the isocenter to be disposed in one straight line, in response to a position of the radiation source changing in response to the rotation of the C-arm.

5. The blood vessel image processing method of claim 1, wherein
    the computing of the target distance comprises computing the target distance based on the first vertical distance, the second vertical distance, and a projection angle of the radiation.

6. The blood vessel image processing method of claim 5, wherein
    the projection angle of the radiation is an angle between an axis orthogonal to a plane comprising a surface of the table and an axis corresponding to a projection direction of the radiation.

7. The blood vessel image processing method of claim 5, wherein
    the computing of the target distance comprises:
    computing a first value by subtracting the second vertical distance from the first vertical distance;

computing a second value by dividing the computed first value by a cosine value of the projection angle of the radiation; and computing the target distance as a value obtained by subtracting the computed second value from a straight line distance from the radiation source to the isocenter.

8. The blood vessel image processing method of claim 1, wherein the radiation source rotates based on at least one of a first rotation axis parallel to the table plane while comprising the isocenter or a second rotation axis different from the first rotation axis, based on the rotation of the C-arm.

9. The blood vessel image processing method of claim 1, wherein the computing of the physical distance of the target blood vessel comprises computing a calibration factor based on the computed target distance.

10. The blood vessel image processing method of claim 9, wherein the computing of the calibration factor comprises computing the calibration factor as a value computed by multiplying, by an imager pixel spacing, a value computed by dividing the computed target distance by a distance from the radiation source to an image receptor.

11. The blood vessel image processing method of claim 9, wherein the computing of the physical distance of the target blood vessel comprises computing a physical distance corresponding to a diameter of the target blood vessel, by multiplying the computed calibration factor by a number of pixels corresponding to the diameter of the target blood vessel shown in the captured blood vessel image.

12. An electronic device for processing a blood vessel image, the electronic device comprising:

a C-arm having an arc shape open toward an isocenter;

a radiation source connected to the C-arm to emit radiation to a target blood vessel located on a table; and a processor configured to compute a target distance from the radiation source to the target blood vessel, based on a first vertical distance from the isocenter to the table and a second vertical distance from the target blood vessel to the table, and compute a physical distance of the target blood vessel using the computed target distance from a blood vessel image captured using the radiation.

13. The electronic device of claim 12, wherein the isocenter is a center of a rotation trajectory of the radiation source generated in response to a rotation of the C-arm.

14. The electronic device of claim 12, wherein the table moves for the radiation source, the target blood vessel, and the isocenter to be disposed in one straight line.

15. The electronic device of claim 14, wherein the table moves together for the radiation source, the target blood vessel, and the isocenter to be disposed in one straight line, in response to a position of the radiation source changing in response to the rotation of the C-arm.

16. The electronic device of claim 12, wherein the processor is configured to compute the target distance based on the first vertical distance, the second vertical distance, and a projection angle of the radiation.

17. The electronic device of claim 16, wherein the projection angle of the radiation is an angle between an axis orthogonal to a plane comprising a surface of the table and an axis corresponding to a projection direction of the radiation.

18. The electronic device of claim 16, wherein the processor is configured to:

compute a first value by subtracting the second vertical distance from the first vertical distance, compute a second value by dividing the computed first value by a cosine value of the projection angle of the radiation, and compute the target distance as a value obtained by subtracting the computed second value from a straight line distance from the radiation source to the isocenter.

19. The electronic device of claim 12, wherein the radiation source rotates based on at least one of a first rotation axis parallel to the table plane while comprising the isocenter or a second rotation axis different from the first rotation axis, based on the rotation of the C-arm.

20. The electronic device of claim 12, wherein the processor is configured to compute a calibration factor based on the computed target distance.

* * * * *